(12) United States Patent
Jones et al.

(10) Patent No.: US 8,910,359 B2
(45) Date of Patent: Dec. 16, 2014

(54) METHOD OF INSPECTING AND/OR REPAIRING A COMPONENT AND A DEVICE FOR INSPECTING AND/OR REPAIRING A COMPONENT

(75) Inventors: Leonard Jones, Berkeley (GB); Holger Litzenberg, Rangsdorf (DE)

(73) Assignees: Rolls-Royce PLC, London (GB); Rolls-Royce Deutschland Ltd & Co KG, Blankenfeld-Mahlow (DE)

( * ) Notice: Subject to any disclaimer, the term of this patent is extended or adjusted under 35 U.S.C. 154(b) by 350 days.

(21) Appl. No.: 13/498,811

(22) PCT Filed: Oct. 22, 2010

(86) PCT No.: PCT/EP2010/065956
§ 371 (c)(1),
(2), (4) Date: Apr. 20, 2012

(87) PCT Pub. No.: WO2011/051179
PCT Pub. Date: May 5, 2011

(65) Prior Publication Data
US 2012/0204395 A1   Aug. 16, 2012

(30) Foreign Application Priority Data
Oct. 28, 2009   (GB) .................................. 0917828.6

(51) Int. Cl.
*B23P 6/00* (2006.01)
*G01N 21/91* (2006.01)
*G01N 21/954* (2006.01)

(52) U.S. Cl.
CPC .............. *G01N 21/91* (2013.01); *G01N 21/954* (2013.01); *F05B 2260/80* (2013.01)
USPC ....................................................... 29/402.01

(58) Field of Classification Search
CPC ...... G01N 21/954; G01N 21/91; G01N 21/88; G01N 21/8803; G01N 21/8806; F05B 2260/80; F05B 2230/80
USPC ............... 29/402.01, 402.04, 402.06, 402.11, 29/402.18, 407.01, 407.04, 705; 250/461.1, 302, 117; 356/237.2
See application file for complete search history.

(56) References Cited

U.S. PATENT DOCUMENTS 4,869,642 A * 9/1989 Williamson et al. .......... 415/146
5,115,136 A   5/1992 Tomasch
(Continued)

FOREIGN PATENT DOCUMENTS

JP        A-54-45192        4/1979

OTHER PUBLICATIONS

Jan. 26, 2011 Written Opinion of the International Searching Authority issued in International Patent Application No. PCT/EP2010/065956.

(Continued)

*Primary Examiner* — John C Hong
(74) *Attorney, Agent, or Firm* — Oliff PLC

(57) ABSTRACT

A method of inspecting a component in an assembled gas turbine engine includes inserting a boroscope and a conduit through an aperture in a casing of the engine. The conduit has an applicator tip. The boroscope and conduit are directed to the component to be inspected. A dye penetrant is supplied through the conduit to the applicator tip. The applicator tip is arranged to contact the surface of the component and dye penetrant is supplied onto the surface of the component from the applicator tip such that the dye penetrant enters any defects in the surface of the component. The applicator tip includes a porous and malleable member. Light is directed onto the component and the surface of the component is viewed through the boroscope to determine if any defects are present in the surface of the component.

30 Claims, 3 Drawing Sheets

(56) References Cited

U.S. PATENT DOCUMENTS 5,396,525 A 3/1995 Domy et al.
8,096,130 B2 * 1/2012 Morenko ........................ 60/739
2005/0041097 A1 2/2005 Bernstein et al.
2008/0297785 A1 12/2008 Bonningue et al.

OTHER PUBLICATIONS

Jan. 26, 2011 International Search Report issued in International Patent Application No. PCT/EP2010/065956.

* cited by examiner

METHOD OF INSPECTING AND/OR REPAIRING A COMPONENT AND A DEVICE FOR INSPECTING AND/OR REPAIRING A COMPONENT

BACKGROUND

The present invention relates to a method of inspecting and/or repairing a component and a device for inspecting and/or repairing a component and the present invention relates in particular to a method of inspecting and/or repairing a component in an assembled apparatus, more particularly a gas turbine engine.

U.S. Pat. No. 5,115,136 discloses a device for inspecting a component in an assembled apparatus. The device comprises a boroscope and a conduit, the conduit has an applicator tip to supply liquids onto the component to be inspected. This device supplies all liquids, dye penetrant, solvent etc through the same conduit, so there is a possibility of cross-contamination. The conduit is part of the boroscope so there is a possibility that the liquids may contaminate the lens of the boroscope and/or cause damage to the lens of the boroscope. In addition the liquid is sprayed out of the applicator tip and this makes it difficult to control the area of the surface of component to be coated in the dye penetrant in order to prevent contamination of adjacent areas not requiring inspection. The larger the area coated in dye penetrant the greater the amount of solvent subsequently required to remove it and this is a disadvantage because the amount of process chemicals introduced into an assembled apparatus must be restricted to achieve reliable inspection of a component within an assembled apparatus.

SUMMARY

Accordingly the present invention seeks to provide a novel method of inspecting and/or repairing a component which reduces, preferably overcomes, the above mentioned problems.

Accordingly the present invention provides a method of inspecting and/or repairing a component in an assembled apparatus, the method comprising the steps of (a) inserting a boroscope and a conduit through an aperture in a casing of the apparatus, the conduit having an applicator tip (b) directing the boroscope and conduit to a component to be inspected and/or repaired, (c) supplying a liquid through the conduit to the applicator tip, (d) contacting the surface of the component with the applicator tip and supplying the liquid onto the surface of the component, the applicator tip comprising a porous and malleable member and providing a restrictor in the conduit or the applicator tip.

Preferably the method comprises providing a foam or a woven fabric as the porous and malleable member.

Preferably the method comprises providing a sheath, the method comprising retracting the applicator tip into the sheath during steps (a) and (b) and moving the applicator tip out of the sheath during steps (c) and (d).

Preferably the method comprises providing a stop member to limit the movement of the applicator tip out of the sheath during steps (c) and (d).

Preferably step (c) comprises supplying a measured quantity of liquid through the conduit to the applicator tip.

Preferably step (c) comprises supplying the measured quantity of liquid from a syringe.

Preferably step (c) comprises supplying a dye penetrant through the conduit to the applicator tip, step (d) comprises contacting the surface of the component with the applicator tip and supplying the dye penetrant onto the surface of the component from the applicator tip such that the dye penetrant enters any defects in the surface of the component, the method comprises step (e) directing light onto the component and (f) viewing the surface of the component through the boroscope to determine if any defects are present in the surface of the component.

Preferably step (e) comprises directing visible light or ultraviolet light onto the surface of the component.

Preferably the method comprises step (g) of supplying a solvent or an emulsifying agent through a conduit to remove excess dye penetrant from the surface of the component after step (d) and before step (e).

Preferably the method comprises step (h) of supplying a solvent or an emulsifying agent through a conduit to remove surface contaminants from the surface of the component before step (d).

Preferably the method comprises drying the surface of the component after step (g) and before step (e).

Preferably the method comprises drying the surface of the component after step (h) and before step (d).

Alternatively step (c) comprises supplying a solvent or an emulsifying agent through a conduit to remove excess dye penetrant from the surface of the component.

Alternatively step (c) comprises supplying a solvent or an emulsifying agent through a conduit to remove surface contaminants from the surface of the component.

Alternatively step (c) comprises supplying an etchant through a conduit to etch the surface of the component.

Preferably the apparatus comprises an engine.

Preferably the engine is a gas turbine engine, a diesel engine or a petrol engine.

Alternatively the apparatus comprises a nuclear reactor.

Preferably the method comprises attaching the conduit to the boroscope.

The present invention also provides a method of inspecting a component in an assembled apparatus, the method comprising the steps of (a) inserting a boroscope and a conduit through an aperture in a casing of the apparatus, the conduit having an applicator tip (b) directing the boroscope and conduit to a component to be inspected, (c) supplying a dye penetrant through the conduit to the applicator tip, (d) contacting the surface of the component with the applicator tip and supplying the dye penetrant onto the surface of the component from the applicator tip such that the dye penetrant enters any defects in the surface of the component, the applicator tip comprising a porous and malleable member, providing a restrictor in the conduit or the applicator tip, (e) directing light onto the component and (f) viewing the surface of the component through the boroscope to determine if any defects are present in the surface of the component.

The present invention also provides a device for inspecting and/or repairing a component in an assembled apparatus, the device comprising a boroscope and a conduit, the conduit having an applicator tip, means to supply a liquid through the conduit to the applicator tip, the applicator tip comprising a porous and malleable member and a restrictor being provided in the conduit or the applicator tip.

Preferably the applicator tip comprises a foam or a woven fabric as the porous and malleable member.

Preferably the conduit comprises a sheath, the applicator tip being retractable into and movable out of the sheath.

Preferably the conduit comprises a stop member to limit the movement of the applicator tip out of the sheath.

Preferably the conduit is attached to the boroscope.

Preferably the device comprises means to direct light onto the component and means to view the surface of the component through the boroscope to determine if any defects are present in the surface of the component.

The present invention also provides a device for inspecting a component in an assembled apparatus, the device comprising a boroscope and a conduit, the conduit having an applicator tip, means to supply a dye penetrant through the conduit to the applicator tip, the applicator tip comprising a porous and malleable member, a restrictor being provided in the conduit or the applicator tip, means to direct light onto the component and means to view the surface of the component through the boroscope to determine if any defects are present in the surface of the component.

The present invention will be more fully described by way of example with reference to the accompanying drawings in which:

DETAILED DESCRIPTION

Figure 1:
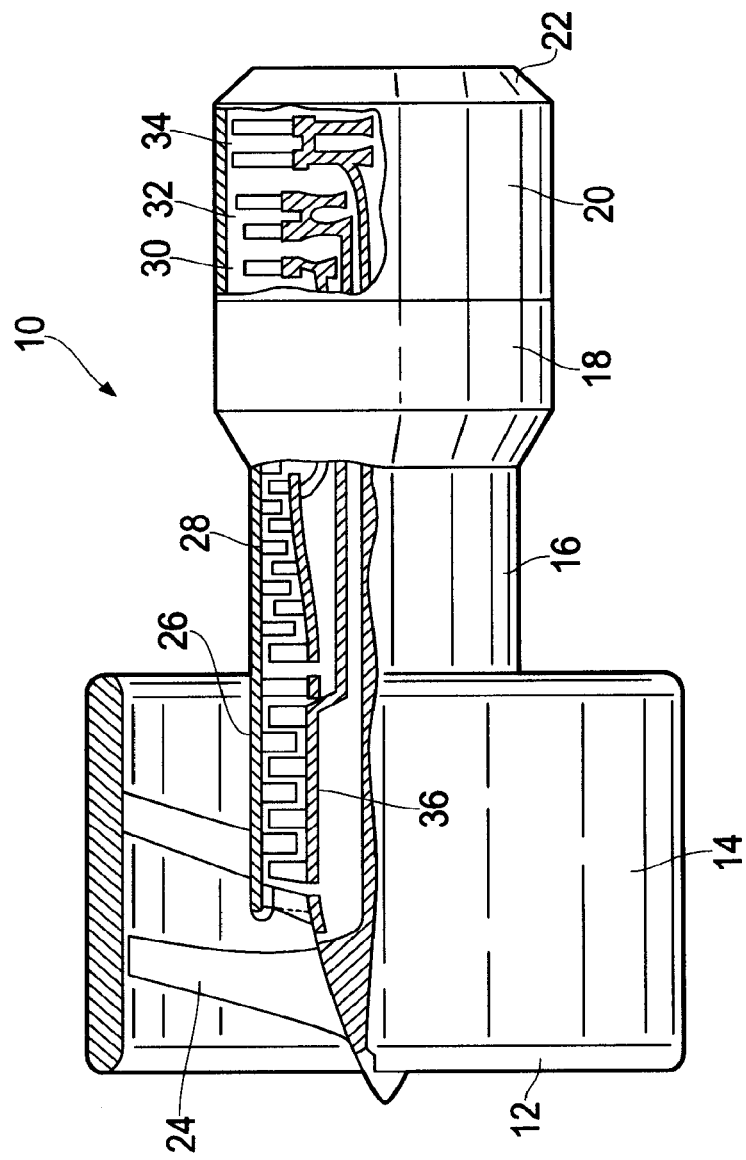
FIG. 1 shows a turbofan gas turbine engine having a component inspected and/or repaired using a method according to the present invention.

A turbofan gas turbine engine 10, as shown in FIG. 1, comprises an inlet 12, a fan section 14, a compressor section 16, a combustion section 18, a turbine section 20 and an exhaust 22. The fan section 14 comprises a fan 24. The compressor section 16 comprises an intermediate pressure compressor 26 and a high pressure compressor 28 arranged in flow series. The turbine section 20 comprises a high pressure turbine 30, an intermediate pressure turbine 32 and a low pressure turbine 34 arranged in flow series. The low pressure turbine 34 is arranged to drive the fan 24, the intermediate pressure turbine 32 is arranged to drive the intermediate pressure compressor 26 and the high pressure turbine 30 is arranged to drive the high pressure compressor 28.

Figure 2:
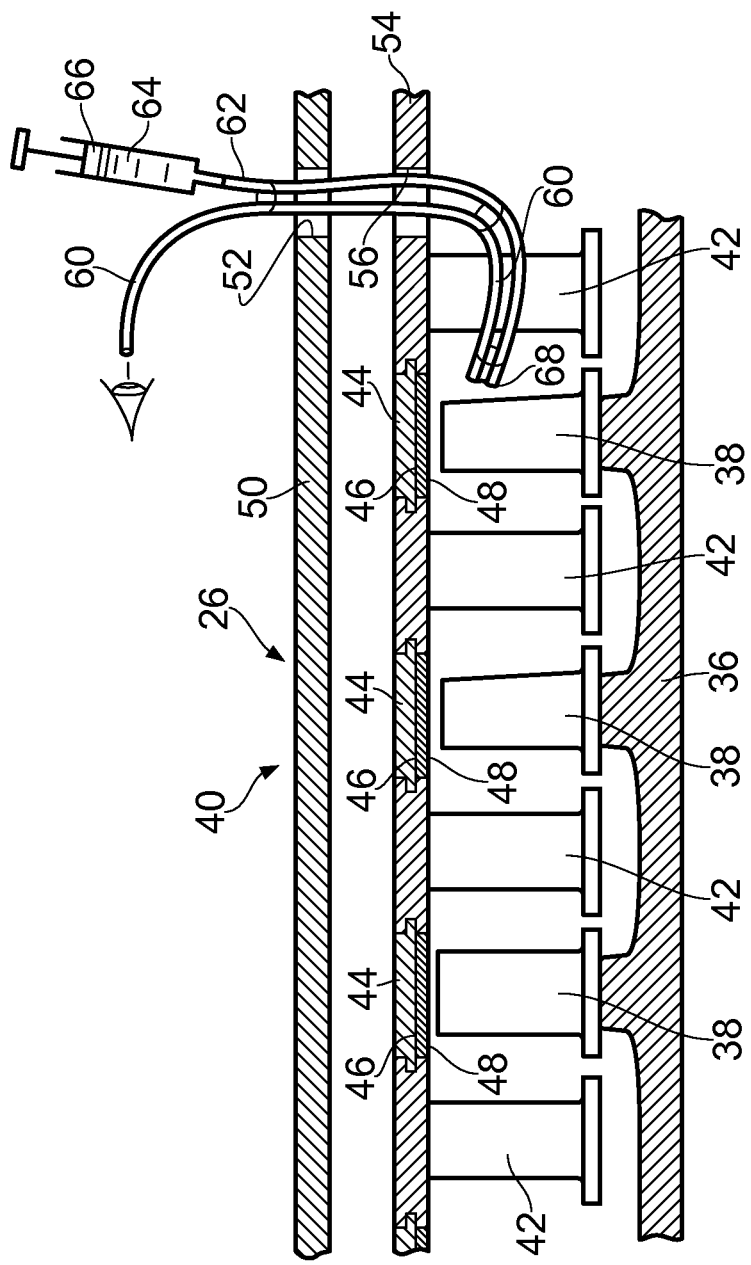
FIG. 2 is an enlarged cross-sectional view through a compressor of the turbofan gas turbine engine having a compressor stator component being inspected and/or repaired using a method according to the present invention.

The intermediate pressure compressor 28, as shown more clearly in FIG. 2, comprises a rotor 36 carrying a plurality of stages of compressor rotor blades 38 and a stator 40 carrying a plurality of stages of compressor stator vanes 42. The compressor rotor blades 38 in each stage are circumferentially spaced and extend generally radially outwardly from the rotor 36. The compressor stator vanes 42 in each stage are circumferentially spaced and extend generally radially inwardly from the stator 40. The stator 40 also comprises a plurality of shrouds 44 interconnecting the stages of compressor stator vanes 42 and the shrouds 44 are positioned radially around a corresponding one of the stages of compressor rotor blades 38. The stator 40 of the intermediate pressure compressor 28 also comprises a casing 50 and the casing 50 is provided with one or more apertures 52 to allow access for boroscopes. In addition the radially outer platforms 54 of one or more of the compressor stator vanes 42 have an aperture 56 to allow access for boroscopes.

The present invention provides a method of inspecting a component generally in an assembled apparatus, in this particular case the assembled gas turbine engine 10. The method comprises the steps of inserting a boroscope 60 through the aperture 52 in the casing 50 of the intermediate pressure compressor 28 of the gas turbine engine 10. The baroscope 60 is also inserted through the aperture 56 in the radially outer platform 54 of one of the compressor stator vanes 42 of the intermediate pressure compressor 38 of the gas turbine engine 10. The boroscope 60 is arranged to carry a conduit 62 and the conduit 62 has an applicator tip 68. The boroscope 60 and hence the conduit 62 are directed, manoeuvred or manipulated, to a component, for example a compressor stator vane 42, a compressor rotor blade 38, etc, within the intermediate pressure compressor 26 to be inspected. A dye penetrant 64 is supplied from a supply 66 through the conduit 62 to the applicator tip 68 of the conduit 62, the applicator tip 68 is arranged to contact the surface of the component 38, 42 and the dye penetrant 64 is supplied onto the surface of the component 38, 42 from the applicator tip 68 of the conduit 62 such that the dye penetrant 64 enters any defects in the surface of the component 38, 42. The applicator tip 68 comprises a porous and malleable member 70. The applicator tip 68 supplies the dye penetrant 64 onto the surface of the component 38, 42 by actually contacting the surface of the component 38, 42 with the applicator tip 68 and moving over the surface of the component 38, 42 as required. Light is directed onto the component 38, 42 and the surface of the component 38, 42 is viewed through the boroscope 60 to determine if any defects are present in the surface of the component 38, 42. Either visible light or ultraviolet light is directed onto the surface of the component 38, 42. The baroscope 60 may be used with ultraviolet and/or white light depending on the particular dye penetrant applied to the component being inspected. The boroscope 60 is able to view components at close to medium distances, e.g. 4 to 15 mm, possibly with interchangeable optics, or lenses, at the tip of the boroscope 60. The light may be introduced by a separate light guide if the boroscope cannot transmit light of the required wavelength there-through to view the surface of the component 38, 42.

An important feature of the present invention is to provide sufficient dye penetrant on the applicator tip 68 so that the dye penetrant is supplied onto the surface of the component 38, 42 when the applicator tip 68 contacts the surface of the component 38, 42, but not too much dye penetrant is supplied to the applicator tip 68 such that the dye penetrant drips from the applicator tip 68 when the applicator tip 68 does not contact the surface of the component 38, 42. To facilitate the achievement of these objectives, a restriction may be provided at the end of the conduit 62 by partially inserting the porous and malleable member 70 into the end of the conduit 62 or by providing, inserting, a smaller diameter tube into the end of the conduit 62. A restriction may not always be required, because the requirement for a restriction depends upon the internal diameter of the conduit 62. In particular for conduits with internal diameters of at least 0.5 mm a restriction is required in the conduit to achieve a neutral flow, but for conduits with internal diameters of at most 0.3 mm no restriction is required in the conduit.

Figure 3:
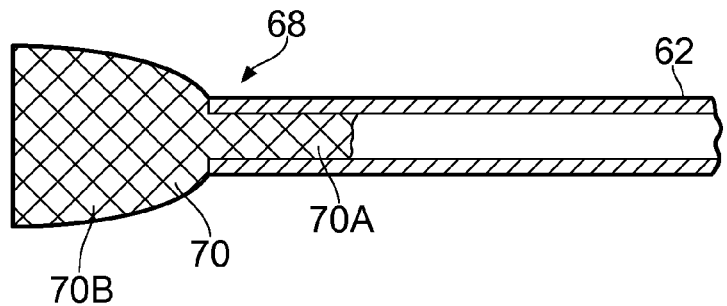
FIG. 3 is an enlarged view of an applicator tip of a conduit for use in the method according to the present invention.

A first applicator tip 68 is shown more clearly in FIG. 3 and the porous and malleable member 70 comprises a foam or a woven fabric secured to and extending from the end of the conduit 62. A first portion 70A of the porous and malleable member 70 is inserted into the end of the conduit 62 to restrict the flow of dye penetrant, as mentioned above, and a second portion 70B of the porous and malleable member 70 protrudes from the end of the conduit 62.

Figure 4:
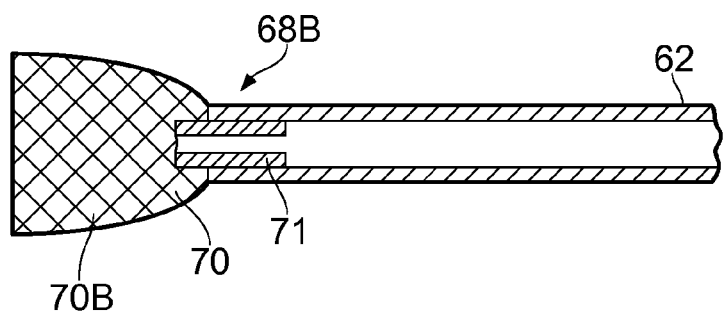
FIG. 4 is an enlarged view of an alternative applicator tip of a conduit for use in the method according to the present invention.

An alternative applicator tip 68B is shown more clearly in FIG. 4 and the porous and malleable member 70 comprises a foam or a woven fabric secured to and extending from the end of the conduit 62. A tube 71 with a smaller internal diameter than the conduit 62 is inserted into the end of the conduit 62 to restrict the flow of dye penetrant, as mentioned above, and the tube 71 protrudes from the end of the conduit 62 into the porous and malleable member 70.

Figure 5:
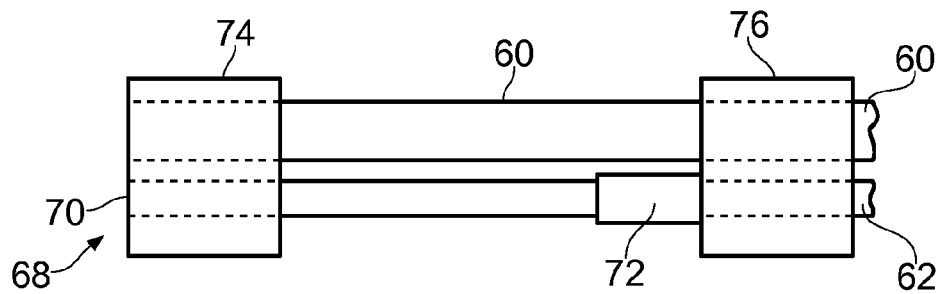
FIG. 5 is an enlarged view of an end of a conduit secured to a boroscope with the applicator tip in an inoperative position.
Figure 6:
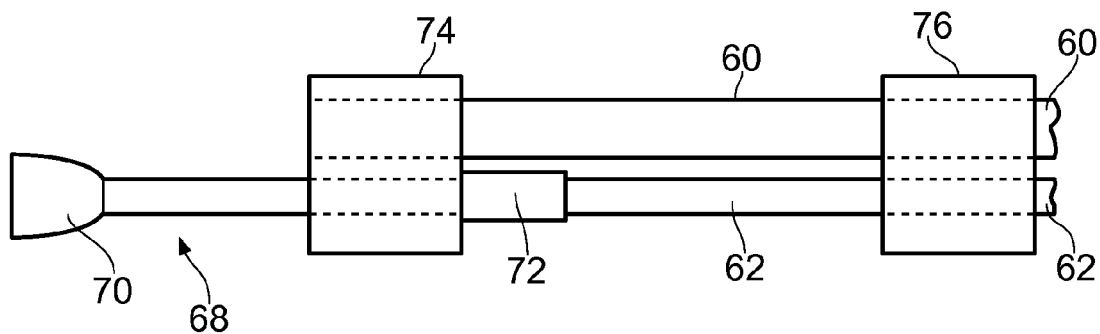
FIG. 6 is an enlarged view of an end of a conduit secured to a boroscope with the applicator tip in an operative position.

In addition a sheath 74 is provided, as shown more clearly in FIGS. 5 and 6. The applicator tip 68 is retractable into the sheath 74 while the boroscope 60 and conduit 62 are directed towards and away from the component 38, 42 to be viewed, as shown in FIG. 5. The applicator tip 68 is movable out of the sheath 74 while the dye penetrant 64 is applied to the surface of the component 38, 42, as shown in FIG. 6. The sheath 74 is secured to the end of the boroscope 60 and secures the conduit 62 to the end of the baroscope 60. A stop member 72 is provided on the conduit 62 to limit the movement of the applicator tip 68 out of the sheath 74 and to lock the applicator tip 68 in position for dispensing dye penetrant 64 onto the surface of a component 38, 42. The stop member 72 moves longitudinally relative to the boroscope 60 between a first position, as shown in FIG. 5, in which the stop member 72 abuts a guide member 76, which holds the conduit 62 onto the boroscope 60, and a second position, as shown in FIG. 6, in which the stop member 72 abuts the sheath 74.

A measured quantity of dye penetrant 64 is supplied through the conduit 62 to the applicator tip 68 and this measured quantity of dye penetrant 64 is supplied in this example from the syringe 66.

If the surface of the component 38, 42 is dirty, or contaminated, it may be necessary to supply a solvent through a conduit, either the same conduit or preferably a different conduit, to remove surface contaminants from the surface of the component 38, 42 before the dye penetrant 64 is supplied onto the surface of the component 38, 42. The conduit has an applicator tip with a porous and malleable member. A measured quantity of solvent is supplied through the conduit and this measured quantity of solvent is supplied in this example from a syringe. The surface of the component 38, 42 may be dried, using air directed onto the surface of the component 38, 40, after the solvent has been used to remove contaminants and before the dye penetrant is supplied onto the surface of the component 38, 42.

After the dye penetrant 64 has been supplied onto the surface of the component 38, 42 it may be necessary to supply a solvent, or an emulsifying agent, through a conduit, either the same conduit or preferably a different conduit, to remove excess dye penetrant 64 from the surface of the component 38, 42. The conduit has an applicator tip with a porous and malleable member. A measured quantity of solvent, or emulsifying agent, is supplied through the conduit and this measured quantity of solvent, or emulsifying agent, is supplied in this example from a syringe. The surface of the component 38, 42 may be dried, using air directed onto the surface of the component 38, 40, after the solvent, or emulsifying agent, has been used to remove excess dye penetrant 64 and before the surface of the component 38, 42 is viewed by the boroscope 60 under visible, or ultraviolet, light. The solvent may be water.

The arrangement is designed to provide a neutral flow of dye penetrant 64 to the porous and malleable member 70 at the applicator tip 68. This has the advantage of controlling and limiting the area of application of the dye penetrant 64 on the surface of the component 38, 42 and the quantity of dye penetrant 64 applied onto the surface of the component 38, 42. The neutral flow of dye penetrant 64 is achieved by the combination of a fluid flow restrictor, provided in the conduit 62, or the applicator tip 68, and variable applied pressure.

A brief summary of the method of inspecting a component is to identify an area of a component, or to identify a component, to be inspected. Clean the surface of the component if necessary. Dry the surface of the component if necessary. Apply dye penetrant to the surface of the component. Allow a suitable time for the dye penetration process to occur, about 10 to 60 minutes. Remove excess dye penetrant from the surface of the component if necessary. Dry the surface of the component if necessary. Allow the self development of any defect indications formed, up to 10 minutes. View under suitable illumination, visible light or ultraviolet light, using the boroscope. Determine the position(s) of any defects, cracks or fissures etc, using accurate measurement techniques.

In some circumstances, such as after metal removal by grinding, reliable inspection of the component may only be achieved if the surface of the component has been etched prior to application of the dye penetrant. A conduit with an applicator tip with a porous and malleable member may be provided to controllably supply etchant to the surface of the component before the dye penetrant.

Any low viscosity liquid may be supplied using a conduit with an applicator tip according to the present invention.

The advantages of the present invention are that each process chemical, e.g. solvent, emulsifying agent, dye penetrant etc is supplied through a respective conduit, which avoids cross contamination. The main advantage is that there is a reduction in contamination of other components etc with dye penetrant because the dye penetrant is applied by contact with the component and not by spraying onto the component. The sheath provides a further reduction in contamination of other components etc with dye penetrant. The use of a contact method of applying the dye penetrant controls the area of application of the dye penetrant and therefore avoids over washing, avoids recontamination from excess dye penetrant, optimises dye penetrant removal and controls the quantity of solvent remover. It enables application of dye penetrant into restricted access areas and thus surface open defects are made more visible by using high contrast dye penetrants which enter the surface open defects and may fluoresce under ultraviolet light and thus the inspection is more sensitive and reliable. The dye penetrant enables the detection of open surface defects and the detection of the length of the open surface defects, e.g. cracks.

Although the present invention has been described with reference to inspecting a component in a compressor of an assembled gas turbine engine, it is equally applicable to inspecting a component in other regions of the gas turbine engine, e.g. the fan, a combustor, a turbine, a gearbox, etc to inspect a stator vane, a stator, a rotor blade, a rotor, a combustor, etc. Although the present invention has been described with reference to inspecting a component in an assembled gas turbine engine, it is equally applicable to inspecting a component in an assembled diesel engine, an assembled petrol engine, an assembled nuclear reactor, an assembled power generator, an assembled aircraft, an assembled marine vessel or any industry where it is necessary to inspect components with non-porous surfaces which have restricted access.

Although the present invention has been described principally with reference to inspecting a component in an assembled apparatus it is equally applicable to repairing a component in an assembled apparatus and the conduit may be used to supply liquids used during the repair of the component. The method of inspecting a component in an assembled apparatus may be an initial step in a method of repairing a component if it is determined, by the inspection process, that the component is damaged and it is necessary to repair the component. Alternatively, if it is determined, by the inspection process, that the component is damaged it may be necessary to replace the component. If it is determined, by the inspection process, that the component is not damaged, or is not significantly damaged, it may not be necessary to repair, or replace, the component. The method of repairing may include machining and/or material deposition, or metal deposition, to repair one or more components. The repair of the rotor blades and/or stator vanes in a compressor and/or a turbine of a gas turbine engine may comprise grinding to remove material to blend the aerofoils to remove the open surface defects, cracks, in the rotor blades and/or stator vanes.

The invention claimed is:

1. A method of inspecting and/or repairing a component in an assembled apparatus, the method comprising the steps of (a) inserting a boroscope and a conduit through an aperture in a casing of the apparatus, the conduit having an applicator tip, (b) directing the boroscope and the conduit to a component to be inspected and/or repaired, (c) supplying a liquid through the conduit to the applicator tip, (d) contacting a surface of the component with the applicator tip and supplying the liquid onto the surface of the component, the applicator tip comprising a porous and malleable member.

2. A method as claimed in claim 1 wherein the method comprises providing a foam or a woven fabric as the porous and malleable member.

3. A method as claimed in claim 1 comprising providing a sheath, the method comprising retracting the applicator tip into the sheath during steps (a) and (b) and moving the applicator tip out of the sheath during steps (c) and (d).

4. A method as claimed in claim 3 comprising providing a stop member to limit the movement of the applicator tip out of the sheath during steps (c) and (d).

5. A method as claimed in claim 1 wherein step (c) comprises supplying a measured quantity of liquid through the conduit to the applicator tip.

6. A method as claimed in claim 1 wherein step (c) comprises supplying the measured quantity of liquid from a syringe.

7. A method as claimed in claim 1 wherein step (c) comprises supplying a dye penetrant through the conduit to the applicator tip, step (d) comprises contacting the surface of the component with the applicator tip and supplying the dye penetrant onto the surface of the component from the applicator tip such that the dye penetrant enters any defects in the surface of the component, the method comprises step (e) directing light onto the component and (f) viewing the surface of the component through the boroscope to determine if any defects are present in the surface of the component.

8. A method as claimed in claim 7 wherein step (e) comprises directing visible light or ultraviolet light onto the surface of the component.

9. A method as claimed in claim 7 wherein the method comprises step (g) of supplying a solvent or an emulsifying agent through a conduit to remove excess dye penetrant from the surface of the component after step (d) and before step (e).

10. A method as claimed in claim 9 wherein the method comprises drying the surface of the component after step (g) and before step (e).

11. A method as claimed in claim 7 wherein the method comprises step (h) of supplying a solvent or an emulsifying agent through a conduit to remove surface contaminants from the surface of the component before step (d).

12. A method as claimed in claim 11 wherein the method comprises drying the surface of the component after step (h) and before step (d).

13. A method as claimed in claim 1 wherein the liquid is a dye penetrant and the step (c) comprises supplying a solvent or an emulsifying agent through a conduit to remove excess dye penetrant from the surface of the component.

14. A method as claimed in claim 1 wherein step (c) comprises supplying a solvent or an emulsifying agent through a conduit to remove surface contaminants from the surface of the component.

15. A method as claimed in claim 1 wherein step (c) comprises supplying an etchant through a conduit to etch the surface of the component.

16. A method as claimed in claim 1 wherein the apparatus comprises an engine.

17. A method as claimed in claim 16 wherein the engine is a gas turbine engine, a diesel engine or a petrol engine.

18. A method as claimed in claim 1 wherein the apparatus comprises a nuclear reactor.

19. A method as claimed in claim 1 wherein the method comprises attaching the conduit to the boroscope.

20. A device for inspecting and/or for use when repairing a component in an assembled apparatus, the device comprising a boroscope and a conduit, the conduit having an applicator tip, means to supply a liquid through the conduit to the applicator tip, the applicator tip comprising a porous and malleable member.

21. A device as claimed in claim 20 wherein the applicator tip comprises a foam or a woven fabric as the porous and malleable member.

22. A device as claimed in claim 20 wherein the conduit comprises a sheath, the applicator tip being retractable into and movable out of the sheath.

23. A device as claimed in claim 22 wherein the conduit comprises a stop member to limit the movement of the applicator tip out of the sheath.

24. A device as claimed in claim 20 wherein the conduit is attached to the boroscope.

25. A device as claimed in claim 20 comprising means to direct light onto the component and means to view a surface of the component through the boroscope to determine if any defects are present in the surface of the component.

26. A method of inspecting and/or for use when repairing a component in an assembled apparatus, the method comprising the steps of (a) inserting a boroscope and a conduit through an aperture in a casing of the apparatus, the conduit having an applicator tip, (b) directing the boroscope and the conduit to a component to be inspected and/or repaired, (c) supplying a liquid through the conduit to the applicator tip, (d) contacting a surface of the component with the applicator tip and supplying the liquid onto the surface of the component, the applicator tip comprising a porous and malleable member and providing a restrictor in the conduit or the applicator tip.

27. A method of inspecting and/or for use when repairing a component in an assembled apparatus, the method comprising the steps of (a) inserting a boroscope and a conduit through an aperture in a casing of the apparatus, the conduit having an applicator tip, (b) directing the boroscope and the conduit to a component to be inspected and/or repaired, (c) supplying a liquid through the conduit to the applicator tip, (d) contacting a surface of the component with the applicator tip and supplying the liquid onto the surface of the component, the applicator tip comprising a porous and malleable member, providing a restrictor in the conduit or the applicator tip and applying a variable pressure.

28. A method as claimed in claim 7 comprising a step of repairing the component if any defects are present in the surface of the component.

29. A method as claimed in claim 28 wherein the step of repairing comprises machining the component.

30. A method as claimed in claim 28 wherein the step of repairing comprises depositing material on the component.

* * * * *